United States Patent
Koehler et al.

(10) Patent No.: US 6,839,620 B1
(45) Date of Patent: Jan. 4, 2005

(54) DETECTING SOOT DURING REAL TIME OPERATION IN DIESEL ENGINE LUBRICANT

(75) Inventors: Charles J. Koehler, Milwaukee, WI (US); Richard W. Hirthe, Milwaukee, WI (US); Martin A. Seitz, Brookfield, WI (US)

(73) Assignee: Eaton Corporation ( * ) Notice: Subject to any disclaimer, the term of this patent is extended or adjusted under 35 U.S.C. 154(b) by 0 days.

(21) Appl. No.: 10/624,756

(22) Filed: Jul. 22, 2003

(51) Int. Cl.$^7$ .............................................. G01N 33/26
(52) U.S. Cl. ............................... 701/108; 73/53.05
(58) Field of Search .................... 701/108; 73/53.05, 73/61.76; 123/376, 452, 463; 324/672, 663

(56) References Cited

U.S. PATENT DOCUMENTS

| | | |
|---|---|---|
| 6,278,281 B1 | 8/2001 | Bauer et al. ............... 324/441 |
| 6,377,052 B1 | 4/2002 | McGinnis et al. .......... 324/446 |
| 6,380,746 B1 | 4/2002 | Polczynski et al. ......... 324/446 |
| 6,513,367 B2 * | 2/2003 | Bondarowicz et al. ..... 73/53.05 |

* cited by examiner

*Primary Examiner*—Hieu T. Vo
(74) *Attorney, Agent, or Firm*—Roger A. Johnston

(57) ABSTRACT

A probe having a pair of closely spaced electrodes is immersed in the lubricant and one electrode is excited with a relatively low voltage AC current. The frequency is swept over a range of about 1–10,000 Hertz and the current and phase angle measured at selected frequency intervals. The reactive (Z") and resistive (Z") impedances are computed for each current measurement and values of Z" plotted as a function of Z' as a Nyquist plot. The center of curvature of the plot between the origin and the minimum value of Z" is located; and, the angle of depression of a line from the origin through the center of curvature Θ is determined from the plot. Samples of lubricant having known concentration of soot are measured and the angle Θ determined for each sample. The angle is then plotted as a function of soot concentration and a smooth curve fitted to the data plots. The curve may be programmed into a microcomputer to be used with the sensor for real time determination of soot concentration.

7 Claims, 3 Drawing Sheets

DETECTING SOOT DURING REAL TIME OPERATION IN DIESEL ENGINE LUBRICANT

BACKGROUND OF THE INVENTION

The present invention relates to detecting the accumulation of soot or carbon particles in diesel engine lubricant. It has been found that recent reductions in mandated limits for vehicle engine exhaust emissions have required fitting diesel engines for use with exhaust gas recirculation (EGR) valves to dilute the fuel-air charge ratio. This has resulted in changes in combustion chemistry and an increase in the rate of build-up of soot blowing past the engine piston rings and contaminating the engine lubricant oil.

The presence of soot above a threshold concentration has been found to render the engine lubricant unable to effectively perform its function and engine damage becomes imminent.

Heretofore, available means for determining soot concentration in engine lubricant were laboratory techniques which required taking a sample of the engine oil to a laboratory for analysis and performing Thermo Gravimetric Analysis or using optical techniques such as Fourier Transform Infrared Spectroscopy to determine the amount of soot present in the lubricant fluid. This has proven to be prohibitively costly and time consuming and thus virtually unworkable when it is necessary to monitor the oil condition of a diesel engine during operation in service.

It is known to use Impedance Spectroscopy in monitoring the condition of engine lubricant fluid during real time operation in engines such as shown and described in U.S. Pat. Nos. 6,278,281, 6,377,052 and 6,380,746. The aforesaid technique utilizes differential Impedance Spectroscopy to detect depletion of the lubricant constituents added by the manufacturer during blending. However the impedance spectroscopy algorithms set forth in the aforesaid patents have been found unable to monitor soot in diesel engine lubricant.

Thus, it has been desired to find a way or means of monitoring diesel engine lubricant during real time operation of the engine and in particular to monitor the concentration of soot.

BRIEF SUMMARY OF THE INVENTION

The present invention utilizes an electrical probe to provide an electrical signal indicative of the soot concentration in the lubricant fluid or oil of a diesel engine during real time operation by employing a novel procedure for analyzing the signal utilizing impedance spectroscopy. An electrical probe having a pair of electrodes is immersed in the lubricant in the engine sump and an alternating current of relatively low voltage of varying frequency is applied to the probe electrodes and the current and phase angle are measured at selected intervals over the range of frequencies. The resistive and reactive components of impedance are then computed and plotted in a Nyquist plot of reactive impedance versus resistive impedance. The center of curvature of the semicircular region of the plot between the origin and the minimum occurring value of reactive impedance is then determined. The angle of depression of the center of curvature from the origin below the X-axis is then computed and plotted for as a function of soot concentration for readings taken with samples of lubricant having a known concentration. An algorithm is then derived from the plot which may be programmed into an electronic controller for comparing the computed depression angle at any given instant with that of known values to determine the corresponding soot concentration at that time.

DETAILED DESCRIPTION OF THE INVENTION

Figure 1:
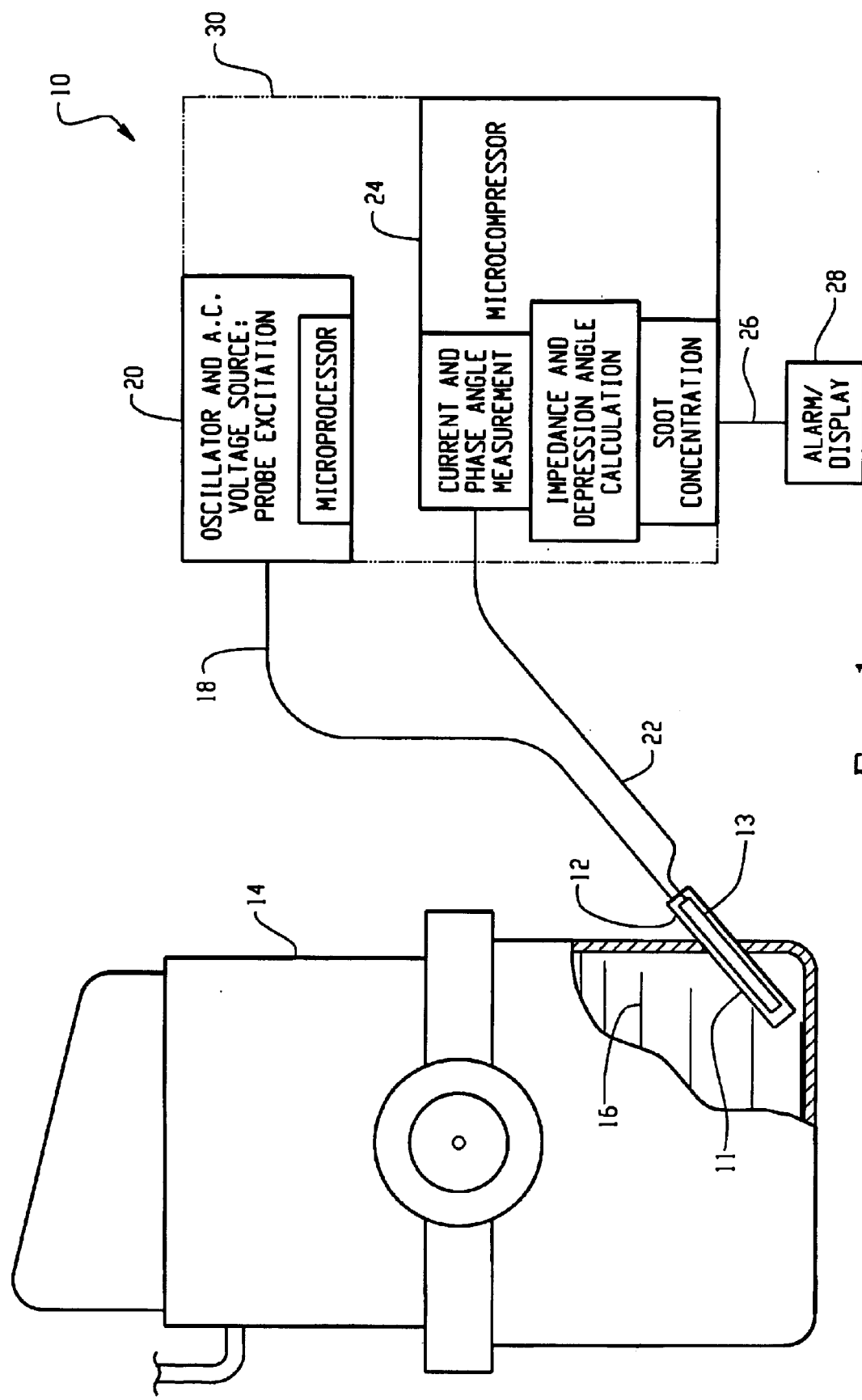
FIG. 1 is a pictorial schematic of a system employing the present invention.

The system of the present invention is indicated generally at 10 and includes a probe 12 inserted into the crankcase or sump of a diesel engine 14 filled with lubricant to a level indicated at 16. The probe may have any suitable electrode configuration; however, in the present practice of the invention it has been found satisfactory to use a pair of concentric tubularly configured concentric electrodes denoted by reference numerals 11, 13 in FIG. 1. This probe may be configured as set forth in co-pending application Ser. No. 10/060,107 filed Jan. 31, 2002, entitled "Probe Assembly For Fluid Condition Monitor And Method Of Making Same" and assigned to the assignee of the present application.

The probe 12 has one electrode excited along line 18 with a relatively low voltage AC current from a controller 20 which may include an oscillator and microprocessor for providing a relatively low voltage source of AC current to the probe. The probe current measured by connection through line 22 to an electronic signal processing unit 24 which may include a microcomputer and which measures the amplitude and phase angle of the current through probe 12 and performs calculations thereon as will hereinafter be described. When the signal processing unit 24 determines that a predetermined threshold condition exists, a signal is sent through line 26 to an alarm/display 28 for alerting the engine operator.

It will be understood that the probe 12 has a pair of electrodes disposed in generally parallel closely spaced arrangement which are immersed in the lubricant in the sump of the engine and that the current measure flows from one electrode through lubricant to the other electrode to complete the current path along lead 22 to the signal processor 24.

It will be understood that the controller 20 and signal processing unit 24 may be located remotely from the engine 14 and combined into a common packaged unit as illustrated in dashed outline in FIG. 1 and denoted by reference numeral 30.

Figure 2:
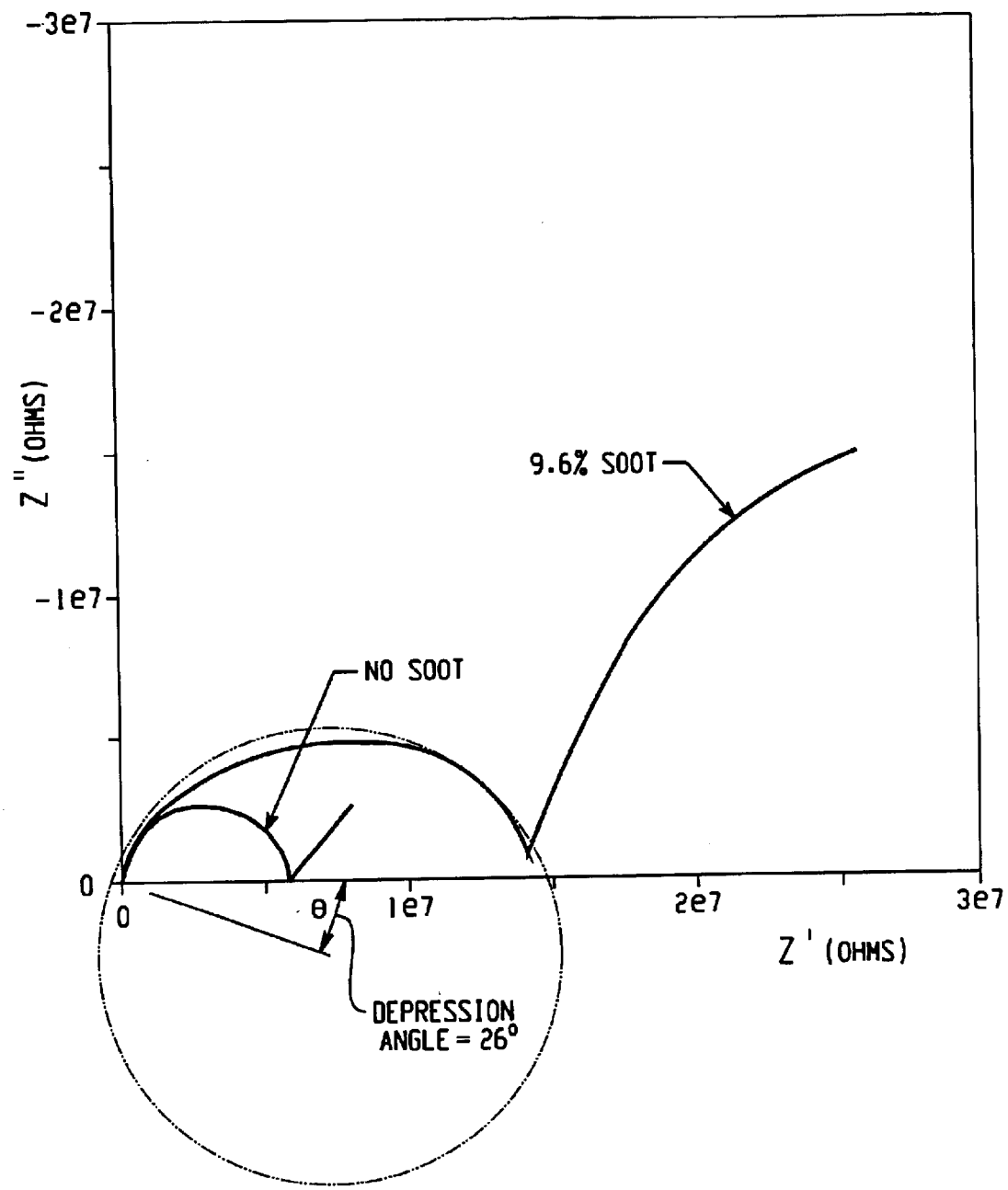
FIG. 2 is a Nyquist plot illustrating the method of determining the depression angle; and, FIG. 3 is a plot of depression angle as a function of soot concentration for two sets of lubricant samples having different known concentrations of soot.

The AC voltage applied to the probe 12 through lead 18 by relatively low voltage excitation as, for example, 1 Volt or less RMS and the frequency is swept over a range of about 1 to 10,000 Hertz. The current and phase angle are measured and, at selected intervals, as for example, intervals of 100–200 Hertz and the reactive impedance and resistive impedance are computed and the data pairs are plotted with the reactive impedance denoted $Z''$ as the ordinates and the resistive impedance denoted $Z'$ as abscissae in a manner known as a Nyquist plot as illustrated in FIG. 2. The center of the semi-circular curvature of the region of the graph between the origin and the minimal value of $Z''$ is then determined from the plots and the angle of depression of the center of curvature formed by a line from the origin through the center of curvature is then computed. The angle of depression is illustrated in FIG. 2 and is denoted by the symbol Θ. The angle of depression is small for diesel engine lubricant containing no soot; and, at a maximum value of about 9.6% soot concentration, the angle of depression Θ has been determined to be about 26 degrees. Thus, the current measurements of the probe may be utilized to determine the percentage of soot concentration in the lubricant because there is enough variation in the depression angle Θ to provide a satisfactory degree of sensitivity or resolution of the sensor to the soot concentration over the range of interest.

Figure 3:
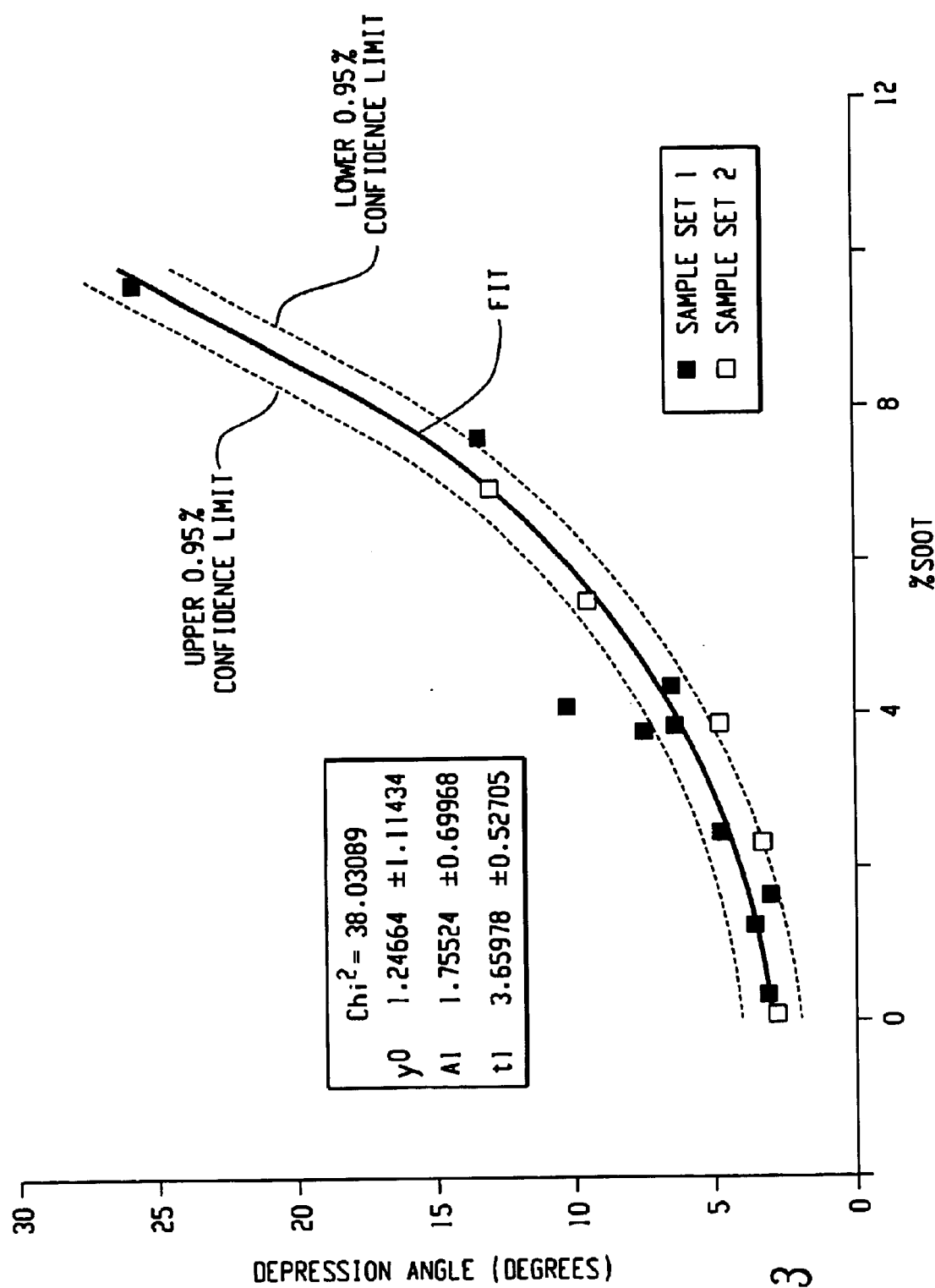

Referring to FIG. 3, the depression angle Θ as measured for two groups of samples of diesel lubricant oil having known concentrations of soot are plotted with the data for each sample set indicated by a distinct legend. The data in each of the two sets of samples were taken separately from lubricant drains from two running engines sequentially at intervals of continuously increasing lubricant stressing. A curve is then fit through the data by any suitable technique as, for example, multiple regression analysis; and, such a curve was fitted and is shown in solid outline, with upper and lower 95% confidence limits shown in dashed outline. It will be seen from FIG. 3 that the technique of the present invention thus permits the use of the depression angle Θ as an analog of the soot concentration and a curve can be generated from measured data. Once the curve has been generated the signal processing unit 24 can be programmed with an algorithm or equation for the curve; and, for a given angle Θ determined from probe current measurements, a corresponding value of percentage of soot determined by the controller.

It will be noted from FIG. 3 that the plotted data from each of the two sets of lubricant drain samples provide a curve with a generally exponential upward curvature. The present invention thus permits measurement of soot concentration in diesel engine oil during operation in real time with a sensor that provides a continuous electrical signal output. The system employing the present invention may be designed as shown in FIG. 1 to have an alarm or display providing a visual or audible indication that the maximum allowable percentage of soot has been reached in the engine lubricant. In the present practice of the invention, it has been found that when the soot concentration in the lubricant reaches a deleterious level it is possible to have the alarm or display set to indicate that the lubricant is no longer capable of effectively performing its function.

Although the invention has hereinabove been described with respect to the illustrated embodiments, it will be understood that the invention is capable of modification and variation and is limited only by the following claims.

What is claimed is:

1. A method of monitoring during real time operation the soot accumulation in diesel engine lubricant comprising:
    (a) disposing a pair of electrodes in the engine lubricant and applying an alternating voltage to the electrode at different frequencies over a selected range and measuring the current magnitude and phase angle at each frequency and computing the resistive and reactive component of the impedance for each current measurement;
    (b) comparing the reactive component as a function of the resistive component of impedance and determining the location of the center of semicircular curvature between the origin and the low frequency minimum occurring value of reactive impedance;
    (c) delaying a specified time interval repeating steps a, b and c computing the angle of depression from the origin to the center of curvature;
    (d) determining the percentage of soot from one of (i) a comparison with known values of percentage soot versus depression angle (ii) a known relationship between percentage soot and depression angle; and,
    (e) providing an electrical signal indicative of soot reaching a selected level of concentration.

2. The method defined in claim 1, wherein said step of providing an electrical signal includes providing a signal which is indicative of soot concentration within a range of about 0–9.6%.

3. The method defined in claim 1, wherein said step of applying an alternating voltage includes applying a voltage over the frequency range associated with bulk fluid impedance measurements.

4. The method defined in claim 1, wherein said step of comparing includes graphing a complex impedance plane (Nyquist) plot.

5. The method defined in claim 1, wherein said step of comparing includes graphing a complex impedance plane (Nyquist) plot and determining the locus of the center of curvature of the Nyquist plot between the origin and the minimum reactance value.

6. The method defined in claim 1, wherein said step of applying an alternating voltage includes applying an alternating voltage and measuring current and phase angle at frequencies over the range of about 1–10,000 Hertz.

7. The method defined in claim 1, wherein said step of comparing includes using computational means.

* * * * *